United States Patent [19]
Eckhoff

[11] Patent Number: 5,669,914
[45] Date of Patent: Sep. 23, 1997

[54] ROTATION ALIGNMENT INSTRUMENT

[75] Inventor: Donald G. Eckhoff, Denver, Colo.

[73] Assignee: Board of Regents of the University of Colorado, Boulder, Colo.

[21] Appl. No.: 602,996

[22] Filed: Feb. 16, 1996

[51] Int. Cl.$^6$ .................................................. A61B 17/56
[52] U.S. Cl. ............................. 606/88; 606/90; 606/102
[58] Field of Search ............................. 606/86, 87, 88, 606/89, 90

[56] References Cited

U.S. PATENT DOCUMENTS

| | | | |
|---|---|---|---|
| 4,501,266 | 2/1985 | McDaniel | 606/90 |
| 4,559,936 | 12/1985 | Hill | 128/92 |
| 4,566,488 | 1/1986 | Rohr, Jr. | 606/88 |
| 4,567,886 | 2/1986 | Petersen | 128/92 |
| 4,653,488 | 3/1987 | Kenna | 606/88 |
| 5,431,653 | 7/1995 | Callaway | 606/90 |
| 5,431,656 | 7/1995 | Clift, Jr. et al. | 606/86 |

OTHER PUBLICATIONS

Biomet Technical Manual, "Intramedullary with Distractor Surgical Technique" (undated).
Coventry, M.B. (1979), "Two–part Total Knee Arthroplasty. Evolution and Present Status," Clin. Orthop. Rel. Research 145:29–36.
Eckhoff, D.G., et al. (1995), "Malrotation Associated with Implant Alignment Technique in Total Knee Arthroplasty," Clin. Orthopaedics and Related Research 321:28–31.
Eckhoff, D.G., et al. (1994), "Version of the Osteoarthritic Knee," J. Arthroplasty 9(1):73–79.
Feng, E.L., et al. (1994), "Progressive Subluxation and Polyethylene Wear in Total Knee Replacements with Flat Articular Surfaces," Clin. Orthop. Rel. Research 299:60–71.
J.N. Insall, et al. (undated) "Principles and Techniques of Knee Replacement", p. 14.

Lewis, P., et al. (1994), "Posteromedial Tibial Polyethylene Failure in Total Knee Replacements," Clin. Orthop. Rel. Research 299:11–17.
Lotke, P.A. and Ecker, M.L. (1977), "Influence of Positioning of Prosthesis in Total Knee Replacement," J. Bone Joint Surgery 59A(1):77–79.
Markolf, K.L., et al. (1976), "Stiffness and Laxity of the Knee—the Contribution of the Supporting Structures," J. Bone Joint Surgery 58A(5):583–594.
Thatcher, J.C., et al. (1987), "Inherent Laxity in Total Knee Prostheses," J. Arthroplasty 2(3):199–207.
Wang, C.J. and Walker, P.S. (1974), "Rotary Laxity of the Human Knee Joint," J. Bone Joint Surgery 56A(1):161–170.
Wasielewski, R.C., et al. (1994), "Wear Patterns on Retrieved Polyethylene Tibial Inserts and Their Relationship to Technical Considerations During Total Knee Arthroplasty," Clin. Orthop. Rel. Research 299:31–43.
Werner, F., et al. (1978), "The Influence of Designs on the Transmission of Torque across Knee Prostheses," J. Bone Joint Surgery 60A(3):342–348.
Whiteside, L.A., et al. (1987), "Varus–Valgus and Rotational Stability in Rotationally Unconstrained Total Knee Anthroplasty," Clin. Orthop. el. Research 219:147–157.

Primary Examiner—Michael Buiz
Assistant Examiner—David O. Reip
Attorney, Agent, or Firm—Greenlee, Winner and Sullivan, P.C.

[57] ABSTRACT

This invention provides a rotation alignment device for aligning the tibia with the femur of a patient prior to placement of prosthetic knee components. The device allows the patient's normal, habitual rotation of the tibia with respect to the femur to be preserved when the prosthesis is placed. It also allows the bones to be moved to any desired position prior to placement of the prosthetic components, including a position dictated by alignment of the long axes of the tibia and femur.

19 Claims, 4 Drawing Sheets

ROTATION ALIGNMENT INSTRUMENT

FIELD OF THE INVENTION

This invention is in the field of medical devices, specifically orthopaedic devices for ensuring femoral and tibial alignment prior to placement of knee prostheses.

BACKGROUND OF THE INVENTION

Excessive wear is a problem in prosthetic knee components where they rotate on each other. Increased conformity between the femoral and tibial implant surfaces where they engage with each other has been recommended to decrease such wear. Increased conformity spreads the load over a greater surface area to decrease bearing stress and the generation of particulate debris. However, this approach presumes that the implants articulate in a hinge-like fashion about a single axis throughout the arc of flexion and extension, rather than taking into account the natural rotation of the knee, especially when the patient's knee is malaligned to begin with, with compensating changes in the surrounding soft tissue.

The natural knee does not operate like hinge moving about a single axis. There is a dynamic external rotation of the tibia on the femur as the knee comes to full extension which is referred to as the screw-home of the knee. This automatic rotation of the tibia reverses on flexion of the knee to produce internal rotation of the tibia on the femur. There is a distinct and separate rotational capacity of the tibia with respect to the femur at each degree of knee flexion which is referred to as rotary laxity of the knee. This rotary laxity allows the tibia to rotate through a limited arc of both internal and external motion at every degree of knee flexion.

These rotational characteristics are considered important components of the kinematics in the natural knee (Markolf, K. L., et al. (1976), "Stiffness and Laxity of the Knee—the Contribution of the Supporting Structures," J. Bone Joint Surgery 58A(5):583–594; Wang, C. J. and Walker, P. S. (1974), "Rotary Laxity of the Human Knee Joint," J. Bone Joint Surgery 56A(1):161–170), despite the fact that discussions of alignment in total knee arthroplasty traditionally focus on axial alignment and do not address rotational alignment (Coventry, M. B. (1973), "Two-part Total Knee Arthroplasty. Evolution and Present Status," Clin. Orthop. Rel. Research 145:29–36; Lotke, P. A. and Ecker, M. L. (1977), "Influence of Positioning of Prosthesis in Total Knee Replacement," J. Bone Joint Surgery 59A(1):77–79).

In total knee arthroplasty, bench studies have documented the rotational laxity and torque transmission of isolated components (Thatcher, J. C., et al. (1987), "Inherent Laxity in Total Knee Prostheses," J. Arthroplasty 2(3):199–207; Werner, F., et al. (1978), "The Influence of Design on the Transmission of Torque across Knee Prostheses," J. Bone Joint Surgery 60A(3):342–348), but the alterations in rotation imparted by rotational malalignment of implanted components in situ have not been clearly defined in the prior art.

In an extensive literature review, the one study identified addressing rotary laxity and screw-home in cadaveric total knee arthroplasties reported that the "screw-home mechanism was unpredictable" and "abnormal in eight of twelve rotation tests, but the authors then came to the contradictory conclusion that the "normal screw-home mechanism was restored" following arthroplasty (Whiteside, L. A., et al. (1987), "Varus-Valgus and Rotational Stability in Rotationally Unconstrained Total Knee Arthroplasty," Clin. Orthop. el. Research 219:147–157.

Applicants have discovered that following total knee arthroplasty, even in "normal" knees with pre-surgical alignment of the long axes of the tibia and femur using contemporary alignment techniques and instruments there will be external rotation of the tibial component relative to the femoral component. In the osteoarthritic knee, there is an average five degrees of external tibial rotation with respect to the femur in the osteoarthritic knee which often leads to additional external rotation of the tibial component relative to the femoral component (Eckhoff, D. G., et al. (1994), "Version of the Osteoarthritic Knee," J. Arthroplasty 9(1):73–79). This malrotation will cause implant wear over time. The findings are confirmed by examination of retrieved tibial polyethylene inserts where the wear pattern is typically posterior-medial and anterior-lateral along the tibial eminence (Feng, E. L., et al. (1994), "Progressive Subluxation and Polyethylene Wear in Total Knee Replacements with Flat Articular Surfaces," Clin. Orthop. Rel. Research 299:60–71; Lewis, P., et al. (1994), "Posteromedial Tibial Polyethylene Failure in Total Knee Replacements," Clin. Orthop. Rel. Research 299:11–17; Wasielewski, R. C., et al. (1994), "Wear Patterns on Retrieved Polyethylene Tibial Inserts and Their Relationship to Technical Considerations During Total Knee Arthroplasty," Clin. Orthop. Rel. Research 299:31–43).

A number of implant alignment techniques are known to the art, including the tibial tubercle alignment technique involving pointing the imaginary front-center of the implant at the tubercle; the posterior-tibial alignment technique involving orienting the implant to the axis defined by the two most posterior points of medial and lateral tibial condyles; the transtibial alignment technique involving positioning the long axis of the component parallel to the imaginary bisector to the tibial plateau to provide maximal coverage of the plateau; the malleolar alignment technique involving orienting the tibial component relative to the malleolar axis defined by the line joining the two most distant points of the medial and lateral malleoli; and the range of motion technique relying on the tibial implant seeking its own rotational alignment as the knee is placed through a range of motion (Eckhoff, D. G., et al. (1995), "Malrotation Associated with Implant Alignment Technique in Total Knee Arthroplasty," Clin. Orthopaedics and Related Research 321:28–31).

Applicants have found, however, that following surgery, all these techniques result in malalignment in varying degrees: 19 degrees for the tibial tubercle method, 5 degrees for the transtibial method, 7 degrees for the posttibial axis method, 3 degrees for the malleolar axis method and 14 degrees for the range of motion method.

A method and apparatus is therefore needed for aligning the femoral and tibial components of a prosthetic knee which takes into account the natural alignment or malalignment of the patient's knee before surgery. If the alteration of rotation occurring in normal knees after arthroplasty is not taken into account and the patient continues with natural, habitual rotational movements of the knee after surgery, the conforming concave and convex surfaces of the prosthetic components will grind on each other, causing excessive wear. This problem is compounded when the patient's knee is malaligned to begin with. In that case, lining up the vertical axes of the bones will lead to an even greater degree of malrotation after surgery since the patient's soft tissues and habits of movement are designed to produce rotation of a different structure than that provided by the prosthesis.

Prior art devices used for arthroplastic alignment include two laminar spreaders as described in J. N. Insall, et al. (undated) "Principles and Techniques of Knee Replacement, p. 14; the Biomet distractor described in Biomet Technical Manual, "Intramedullary with Distractor Surgical Technique" (undated) which fails to provide a stabilizing ledge for aligning with the anterior femoral surface, fails to provide a space to accommodate the anterior cruciate ligament, so that it must be cut before using the distractor, and fails to provide a tibial cutting guide component; the spacer guide described in Petersen U.S. Pat. No. 4,567,886 issued Feb. 4, 1986 having an L-shaped base and a squaring jig but no means for separately adjusting the tension on the ligaments at both sides of the knee; the intramedullary alignment guide described in Clift, Jr. et al. U.S. Pat. No. 5,431,656 requiring an intramedullary bore in the tibia but, again, no means for separately tensioning the ligaments; and the distraction device with spacer block described in Callaway U.S. Pat. No. 5,431,653 which does not provide means for separately tensioning the ligaments. However, none of these devices address a patient's natural rotation.

SUMMARY OF THE INVENTION

This invention provides a rotation alignment device for aligning the tibia with the femur of a patient prior to placement of prosthetic knee components. The device allows the patient's normal, habitual rotation of the tibia with respect to the femur to be preserved when the prosthesis is placed. It also allows the bones to be moved to any desired position prior to placement of the prosthetic components, for example, the position dictated by alignment of the long axes of the tibia and femur.

The device is in the form of a jig with ends designed to move apart from each other to push and hold the tibia away from the femur and put tension on the surrounding ligaments. The device comprises four leaves, two of which are placed against the patient's femur, leaving a space for the anterior cruciate ligament. The other two ends are designed to be moved away from the first two, pushing the tibia away from the femur, and are separately movable so that the tension on each can be separately adjusted and the distance each moves can be separately adjusted. For example, the tension on each side can be equalized so that the normal, habitual rotation of the patient's bones can be preserved when the prosthesis is placed. If the tension on each side is not equalized, even if the tibia is cut to form a rectangular space, after cutting, the ligaments will deform the space and make insertion of the prosthesis difficult. Or, the ligaments will exert rotational force against the prosthesis components and cause excess wear. With the device of this invention, after appropriate alignment is obtained, a rectangular space may be created by bone resection.

More specifically, the device comprises:

a femoral component having femoral leaves separated by a space large enough to accommodate the patient's anterior cruciate ligament, the femoral leaves being in the form of plates having proximal and distal surfaces, the proximal surfaces adapted to abut a patient's distal femur in use;

tibial leaves corresponding to the femoral leaves also being in the form of plates cooperatively engaged with the femoral component and having flat proximal surfaces parallel to the distal surfaces of the femoral leaves; and means for adjusting and maintaining a desired distance between the distal surface of each femoral leaf and the proximal surface of the corresponding tibial leaf.

The femoral component is designed for placement next to the patient's distal femur when the device is in use, and is a component having two projecting femoral leaves which are designed to be placed abutting the distal end of the femur. The distal femur has preferably been previously prepared by cutting flat anterior and distal surfaces thereon. The device is positioned with its projecting femoral ledge abutting the anterior surface so that it can be properly rotationally aligned, and with its femoral leaves abutting the flattened distal surface for proper axial alignment. The two femoral leaves are separated from each other by an inlet in the material of the femoral component, or a space, large enough to allow the femoral leaves to be placed on either side of the patient's anterior cruciate ligament so that the ligament does not have to be cut prior to alignment of the bones. Cutting the ligament at this point is undesirable as it obscures the normal, habitual alignment of the patient's knee components.

The femoral leaves are preferably in the form of plates which are flat or approximately flat. The femoral leaves are defined as having proximal surfaces for placement abutting the distal end of the femur, the opposite surfaces of the plates being defined as the distal surfaces. Both surfaces are preferably flat, although they may be contoured if desired.

The tibial leaves are preferably separate from each other rather than being provided in a single component. The tibial leaves must, in any event, be separately movable in a plane normal to the plane of the leaves. The tibial leaves are designed to abut the proximal surface of the tibia when the device is in use. Preferably they are approximately the same size and shape as the femoral leaves. When the device is not in use, the tibial leaves are attachable to the femoral component in such a way as to each lie parallel and adjacent to its corresponding femoral leaf. The term "corresponding leaf" means the leaf abutting a leaf when the device is not in use.

The tibial leaves are cooperatively engaged with the femoral leaves by means which allow them to move apart from the femoral leaves, and which allow for the movement to be controlled by the operator so that each tibial leaf can be separately moved a desired distance, or so that a desired force can be separately exerted on each. The device of this invention should be capable of applying up to about 30 pounds of force, and achieving a separation adjustable to accommodate from about 8 mm to about 35 mm of total tibial replacement.

Many means are known to the art for communicating force to a device component. Preferably, the tibial leaves are adjustably attached to the femoral leaves by means of a shaft and sheath arrangement which allows movement of the tibial leaves by pushing on shafts or sheaths connected to the tibial leaves, preferably by exerting force on the tibial leaves via a spring. Other mechanisms known to the art could also be used including ratchet mechanisms, lever arms and pneumatic devices.

The means for adjusting and maintaining the desired distance between each tibial leaf and its corresponding femoral leaf may be any known to the art. Preferably, a manual force is exerted against springs which push against the tibial leaves, although the force may also be automated and automatically measured and controlled. When the force is exerted manually, it may be done through a variety of mechanisms known to the art, and is preferably done by turning knobs attached to threaded shafts which communicate pressure through springs against the tibial leaves and allow adjustment and maintenance of the desired pressure. Preferably the threaded shafts move within a threaded sheath attached to the femoral component of the device, and communicate force to structures such as leg barrels attached to the tibial component. The amount of force is measured by calibrated shafts attached to the tibial leaves, or it may be measured by other means known to the art. Preferably the calibrated shafts are disposed within, running through the central channel of, the threaded shafts and/or sheaths of the femoral component.

Once the desired force has been exerted or the desired leaf separation distance achieved as measured by a calibration post between the femoral and tibial leaves, retention means as known to the art may be used to keep the tibial leaves from moving back toward the femoral leaves. The desired distance each tibial leaf is moved may be determined by equalizing the force exerted against each tibial leaf or equalizing the distance between each leaf, or by other criteria such as the alignment techniques discussed above, e.g., aligning the long axes of the bones.

When the tibial leaves are cooperatively engaged with the femoral component, it is desirable that means be provided for preventing them from falling out before being inserted between the patient's bones. If one of the leaves falls out, it must be re-sterilized prior to use. Such means include any known to the art such as catches, clips and the like, and preferably include a keyway such as a groove on the outer surface of a shaft of the tibial leaf component engaging with a key such as a raised bump on the inner surface of a sheath on the femoral component. The shaft or barrel of each tibial leaf is inserted into the sheath of the corresponding femoral leaf turned 180° from its desired final position with the leaves abutting each other. The keyway in the tibial component shaft engages with the bump on the raised surface of the femoral component. As the tibial shaft slides into the sheath, the bump slides along the keyway until the keyway abruptly makes a right angle turn and runs around the circumference of the shaft to a point 180° from the first turn, where it again makes a right angle turn and continues upward. Thus the operator must turn the tibial leaf 180° after it has been slid partway into the sheath, then continue sliding the shaft into the sheath until the leaves abut.

In a preferred embodiment, the femoral component comprises a ledge at approximately right angles to the femoral leaves, and projecting upward at a distance from the end of the leaves sufficient to allow the ledge to rest against a flattened anterior distal femoral surface while the leaves project inside the joint space. This helps to stabilize the device against the knee while the alignment procedure is conducted. The femoral ledge preferably has a surface of at least about 8 square cm and more preferably between about 9 square cm and about 20 square cm. The placement of the ledge ensures that the leaves will not project too far within the joint space so as to allow rotation of the jig relative to the femur. The leaves should project no more than about 4 cm so as to avoid pushing against posterior structures such as the capsule, and preferably between about 3 and about 3.5 cm past the femoral ledge.

It is also important that the distance between the femoral ledge and other structures (such as sheaths or shafts projecting at right angles therefrom at the opposite side of the ledge from the ends of the femoral leaves) be large enough to accommodate a normal patient's fat and muscle tissue above the knee. This distance should be at least about 6 cm and preferably is between about 8 cm and about 10 cm.

The device of this invention also preferably includes a tibial cutting guide. Once the tibia has been separated from the femur a desired distance and aligned at a desired angle, the proximal surface of the tibia should be flattened, and bone material should be removed to accommodate the prosthetic component. This can be accomplished by using the distal surfaces of the tibial leaves as a cutting guide, but is preferably and more accurately accomplished by using a tibial cutting guide comprising a saw groove into which the bone saw can be inserted.

The tibial cutting guide is preferably attached to the device of this invention, preferably by means connecting it to the femoral component. In a preferred embodiment, the tibial cutting guide is slid onto a post (referred to herein as a "separation post") which is attached to the femoral component by means which allow the cutting guide to be moved forward and backward against the knee, such as a slot in the femoral component through which the post is inserted with a tightening knob attached to prevent backward and forward movement once the desired position of the tibial cutting guide against the patient's anterior tibial cortex has been achieved.

The tibial cutting guide preferably comprises means for preventing rotation on the post, such as a securing knob attached to a pointed shaft which can be turned to exert pressure against the post. In a preferred embodiment, the separation post is calibrated with separation marks from which the width of the space between the distal femur and proximal tibia (after cutting) can be read. In this way, the width of the implant component to be used can be directly determined from reading the position of the tibial cutting guide on the separation post, thus eliminating the need for trying various implant sizes to achieve a fit.

Once the tibial cutting guide is in place with its top surface abutting the tibial leaves and the saw guide groove thus positioned in a plane separated from each femoral leaf by a distance taking into account the desired alignment, the tibial cutting guide component may be attached to the tibia. Any means known to the art may be used for securing the tibial cutting guide to the tibia, such as clamps, screws and the like. Preferably drill bits or headless screws are inserted through screw holes in the tibial cutting guide and into the bone.

A preferred embodiment of the device also includes an alignment rod attached to the device when in use which can be used to provide a guide for visually aligning the long axes of the femur and tibia. Preferably the alignment attachment comprising the alignment rod is attached by means which allow it to be easily removed, such as pins engaging with holes in the femoral component.

The method for preparing a patient's femur and tibia for placement of prosthetic knee components of this invention thus involves using a rotation alignment device comprising femoral and tibial components, and comprises:

placing femoral leaves of the femoral component of the alignment device having parallel femoral and tibial leaves adjacent the patient's distal femur and placing the tibial leaves adjacent the patient's proximal tibia without cutting the patient's anterior cruciate ligament;

separating each femoral leaf from its corresponding tibial leaf a desired distance;

placing a tibial cutting guide component comprising a saw groove adjacent to both tibial leaves and to the patient's anterior tibial cortex; and cutting the patient's tibia with a saw placed in the saw groove.

As discussed above, the desired distance between the tibial and femoral leaves may be determined by equalizing the tension on both tibial leaves, by aligning the long axes of the bones, or by other means known to the art. When the tension on both tibial leaves is the same, it is likely that each tibial leaf will be a different distance from its corresponding femoral leaf. This will preserve the normal, habitual alignment of the patient's knee. On the other hand, when each tibial leaf is separated from its corresponding femoral leaf the same distance, the tension on each side is likely to be different.

After the alignment device has been placed, the width of the prosthetic components required may be determined by reading the separation marks on the separation post. The femoral component and tibial leaves are removed from the patient's and the patient's tibia is prepared to receive the implant by cutting the tibia using the saw guide groove. The tibial prosthesis is then aligned to the guide and anchoring holes are prepared in the tibia, as is known to the art, using a template which fits over the cut tibial surface using the template alignment mark on the tibial cutting guide component. The tibial cutting guide component is then removed from the joint and the prosthetic component inserted into the prepared knee joint.

This invention also comprises a method of making a rotation alignment device for aligning a patient's tibia and femur prior to insertion of prosthetic knee components comprising:

providing a femoral component comprising two femoral leaves separated from each other by an inlet large enough to accommodate a patient's anterior cruciate ligament, and two sheaths, each sheath disposed at an approximate right angle to one of the femoral leaves;

providing two tibial components each comprising a tibial leaf and a shaft at approximately right angles to the tibial leaf;

slidably engaging the shafts of the tibial components with the sheaths of the femoral component, whereby each tibial leaf is adjacent and parallel to a corresponding femoral leaf; and providing each sheath with means for separately moving each tibial leaf a desired distance from its corresponding femoral leaf and maintaining the position of the separated leaves.

BRIEF DESCRIPTION OF THE FIGURES

FIG. 3 also shows the alignment attachment in position for engagement with the femoral component.

DETAILED DESCRIPTION OF THE PREFERRED EMBODIMENTS

Figure 1:
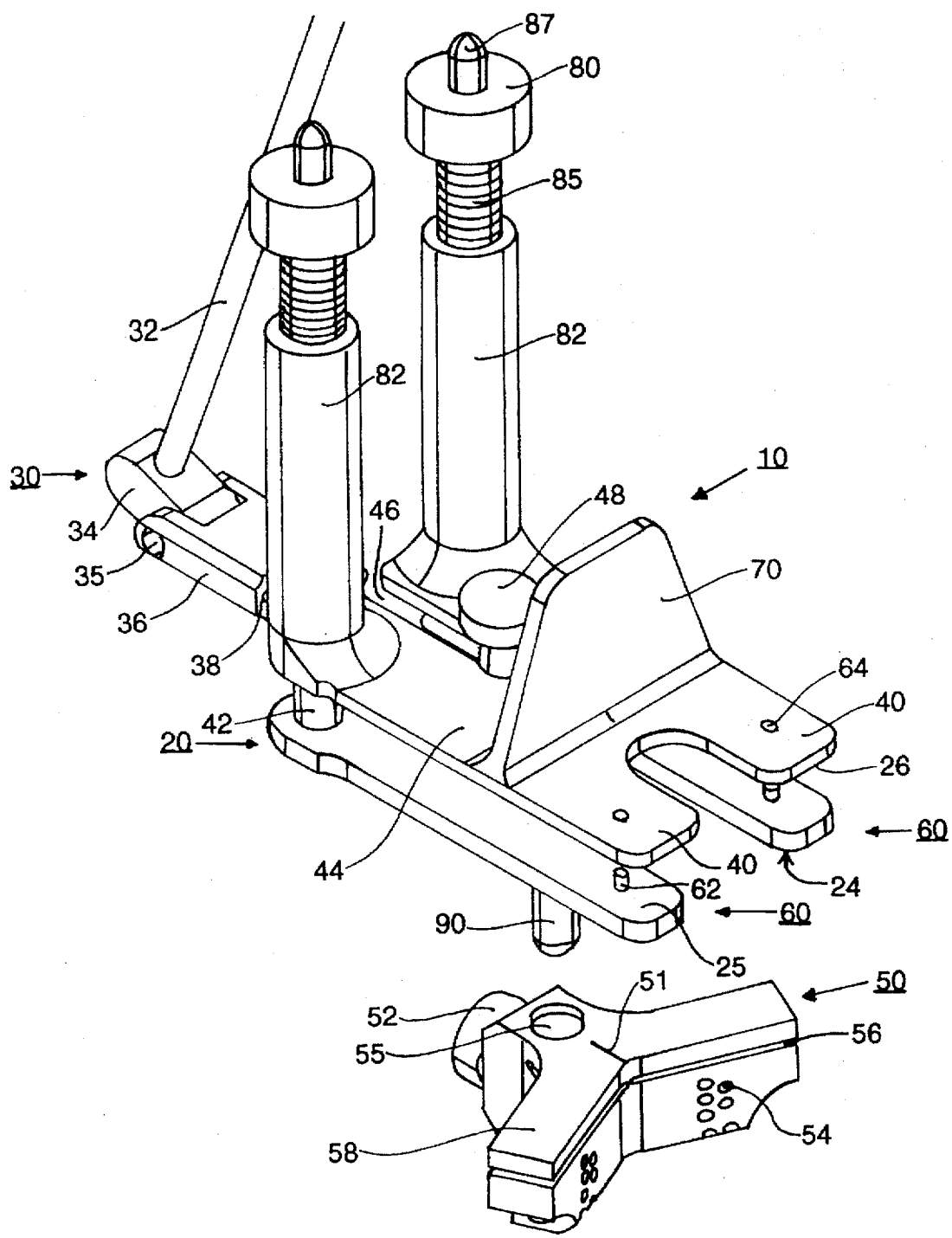
FIG. 1 is a perspective view of the rotation alignment instrument of this invention including the tibial cutting guide component in position for engagement with the femoral component and the alignment attachment engaged with the femoral component.

As shown in FIG. 1, the rotation alignment instrument of this invention comprises a femoral component 10, tibial components 20, and in a preferred embodiment, an alignment attachment 30 and a tibial cutting guide component 50. In the preferred embodiment, the device is made of metal, but as will be appreciated by those skilled in the art, it can also be made of other materials which can be sterilized, such as heat-resistant plastic.

The figures show femoral component 10 comprising two femoral leaves 40 extending outward from a femoral plate 44. The femoral component comprises a femoral plate 44, with two outer sheaths 82 integrally attached to the back end thereof. (The end of femoral plate 44 where the outer sheaths 82 are attached is referred to herein as the back end of the femoral plate.) The femoral plate 44 also comprises two femoral leaves 40 extending in a forward direction as extensions of femoral plate 44. The inner surfaces of the outer sheaths 82 are threaded to receive threaded sheaths 85 which extend from adjustment knobs 80. The femoral component also includes femoral ledge 70 extending at right angles to femoral plate 44 in the same direction as outer sheaths 82 and positioned forward therefrom. Femoral plate groove 46 in femoral plate 44 extends in the forward direction from a point between outer sheaths 82 to femoral ledge 70. Tightening knob 48 slidably engages with femoral plate groove 46 and extends upward from femoral plate 44. Attached to tightening knob 48 on the bottom side of femoral plate 44 is bracket 47 (best seen in FIG. 3) from which separation post 90, bearing separation marks 92, extends downward.

Figure 2:
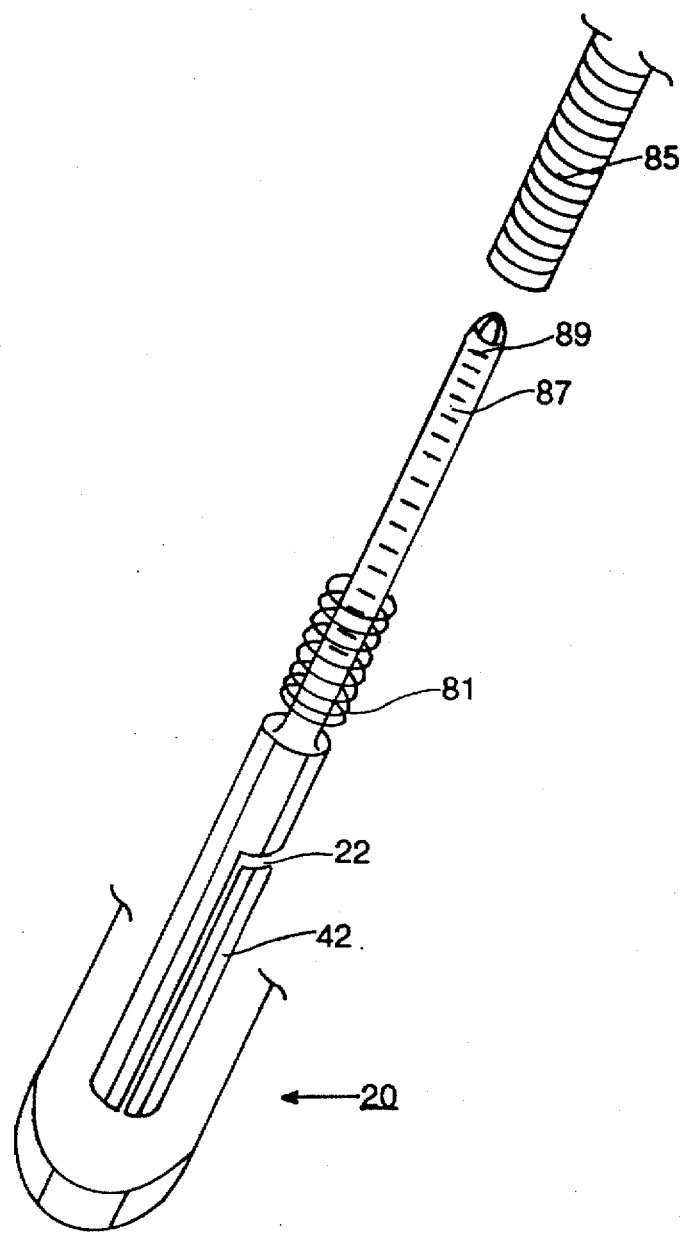
FIG. 2 shows the leg barrel and calibrated shaft of one of the tibial components with keyway, spring and a threaded sheath of the femoral component.
Figure 4:
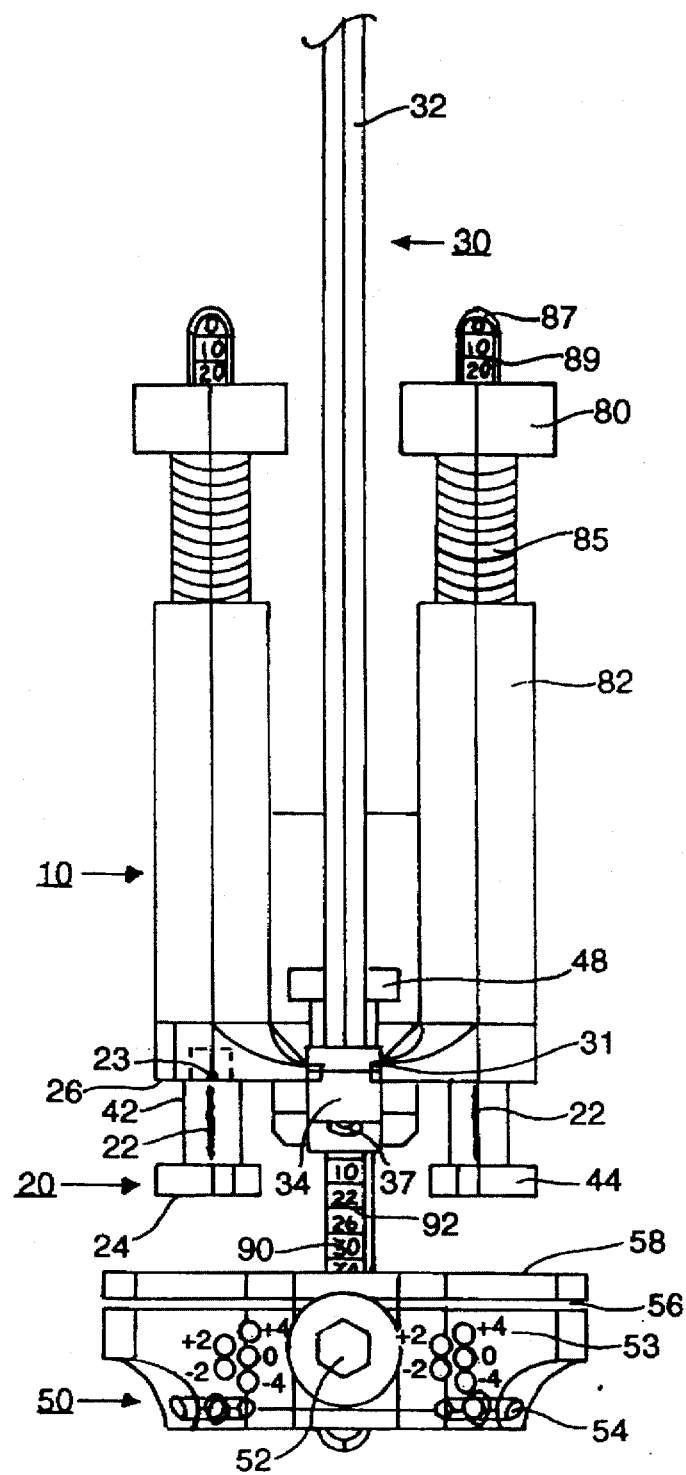
FIG. 4 is a back view of the rotation alignment instrument with all components engaged showing the calibration makes on the calibration shafts and the separation marks on the separation post.

Tibial component 20 comprises separate detachable tibial leaves 60, from each of which leg barrels 42 extend upward at right angles. Disposed within leg barrels 42 and integrally attached thereto are calibrated shafts 87 having calibration marks 89 (best seen in FIG. 4). Tibial leaf proximal surface 25 is equipped with antirotation peg 62 which fits into antirotation hole 64 in femoral leaf 40 when the device is ready for use. As best seen in FIG. 2, leg barrel 42 is equipped with vertical keyway 22 on its front outer surface engagable with a raised key 23 (see cutaway portion of FIG. 4) on the back inner surface of outer sheath 82.

Within outer sheath 82 is disposed threaded shaft 85 which bears on spring 81, through which calibrated shaft 87 extends upward, as seen in FIG. 2.

Figure 3:
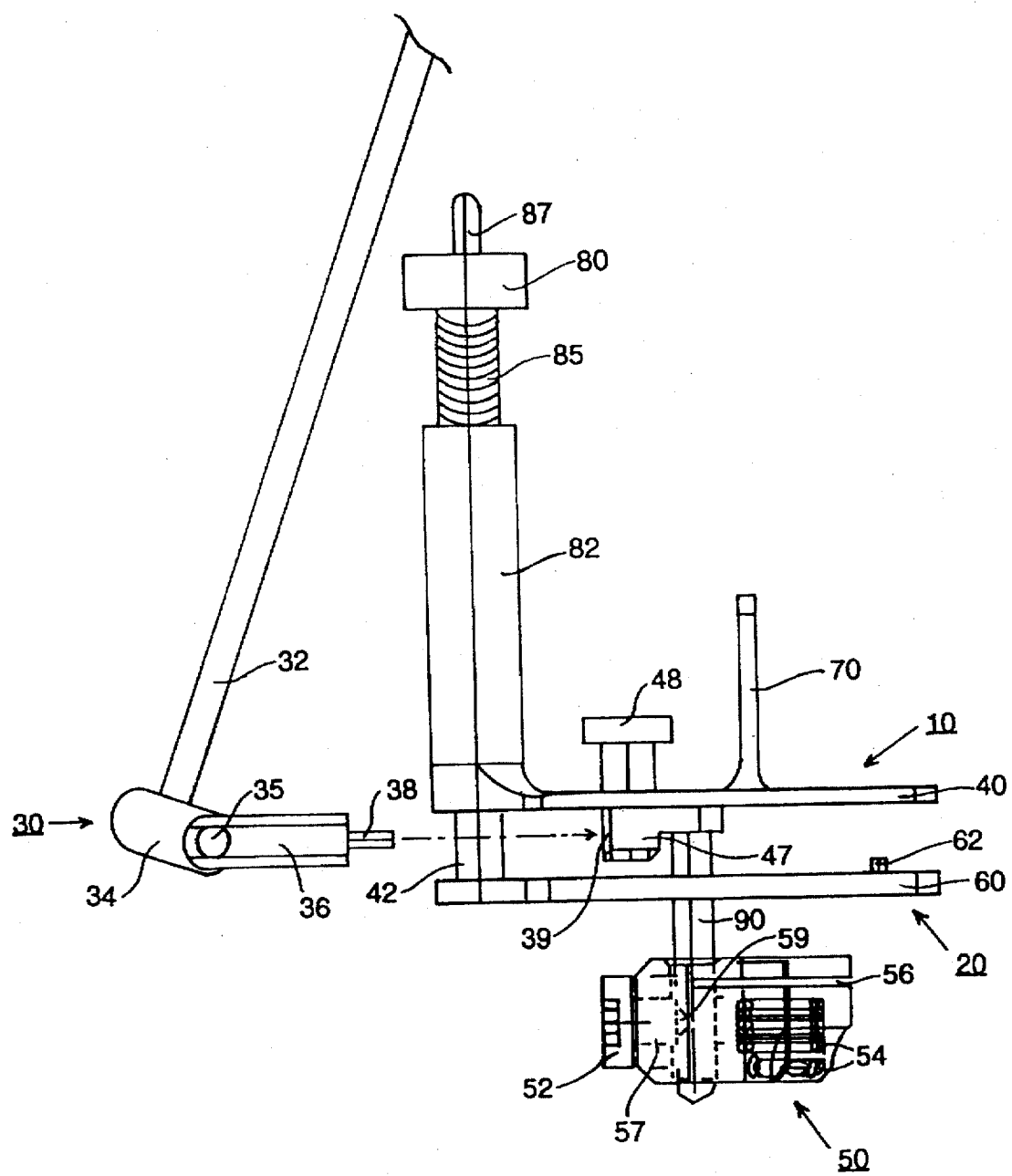
FIG. 3 is a side view of the rotation alignment instrument of this invention showing the tibial cutting guide engaged with the femoral component and indicating internal structures of the tibial cutting guide with dotted lines.

Tibial cutting guide component 50 is perforated with mating bore 55 into which fits separation post 90. As seen in FIG. 3, securing knob 52 is integrally attached to securing shaft 57 which ends in securing point 59 and can be tightened onto the flat side of separation post 90 to hold tibial cutting guide component 50 in place. Tibial cutting guide component 50 is also equipped with saw guide groove 56 and drill holes 54. The drill holes are marked with millimeter markings 53 for positioning the tibial cutting guide component 50 with respect to the tibia. Tibial cutting guide component 50 is marked with template alignment mark 51 for use in aligning a template (not shown) for making anchoring holes in the cut surface of the tibia to aid in placement of the prosthesis.

Optional alignment attachment 30 comprises alignment rod 32 and alignment pivot 34 pivotally attached to alignment rod base 36 by means of circular depressions on the sides thereof pivotally engaging with corresponding tabs 31 on alignment rod base 36 which has two insertion pins 38 projecting therefrom on the opposite side of the base from the pivot, for insertion into pin receiving holes 39 on bracket 47 (as seen in FIG. 3). Alignment pivot has alignment rod hole 37 pierced therethrough for alignment rod 32 to slide in. The ends of alignment rod 32 are equipped with small pegs (not shown) to prevent alignment rod 32 from falling through alignment rod hole 37.

To use the rotation alignment instrument of this invention, the leg barrels 42 of tibial leaves 60, comprising calibrated shafts 87 are inserted into outer sheaths 82 of femoral component 10. To insert the leg barrels 42, the tibial leaves 60 should be facing backward so that the keyway 22 engages with key 23. After the leg barrels 42 have been inserted into outer sheaths 82 for some distance, the keyway 22 makes a right angle turn on its leg barrel 42 as shown in FIG. 2, and proceeds horizontally around the leg barrel 42 to a point 180° from the starting point. The operator must then turn the tibial leaves 60 180° so that the tibial leaves 60 face forward, lining up with the femoral leaves 40. The keyway 22 then again makes a right angle turn and proceeds upward so that the leg barrel 42 can be slid farther into the outer sheath 82. The tibial leaves 60 are thereby kept from falling out. Antirotation peg 62 on each tibial leaf 60 is then engaged with antirotation hole 64 on each femoral leaf 40 to prevent the tibial leaves 60 from rotating with respect to the femoral leaves 40.

The anterior femur at the knee is prepared by removing bone to make a flat anterior surface for femoral ledge 70 to rest against. The anterior portion of the distal femur is also cut at right angles to this flat anterior surface to provide a place for the femoral leaf distal surface to rest. Both the femoral leaves 40 and tibial leaves 60 are now inserted into the knee joint with the patient's leg extended and the adjustment knobs 80 and outer sheaths 82 pointing upward along the patient's leg. At this point, the patient's anterior cruciate ligament is still in place.

Adjustment knobs 80 are now tightened, moving threaded sheaths 85 inward into outer sheaths 82 and depressing springs 81, exposing the top ends of calibrated shafts 87. Adjustment knobs 80 are tightened by hand until the tension on each is equal according to calibration marks 89. The instrument is capable of applying up to about 30 pounds of ligament tension.

Once the tension on each side has been equalized, the tibial cutting guide component 50 is slid onto separation post 90 which is movable in femoral plate groove 46. The tibial guide proximal surface 58 abuts the tibial leaf distal surfaces. Tibial cutting guide component 50 can freely rotate on separation post 90 so that it can be pushed into place against the anterior tibial cortex. At that point, tightening knob 48 is secured so that tibial cutting guide can no longer move forward and backward, and securing knob 52 is tightened so that securing point 59 presses on separation post 90 and prevents further rotation.

Drill bits (not shown) which may be headless screws can then be placed through drill holes 54 and into the tibial bone to hold tibial cutting guide component 50 in place.

A bone saw is then inserted in saw guide groove 56 and the top surface of the tibia is cut to form a flat surface parallel with the tibial leaf distal surfaces 24 of the device. The separation marks 92 on separation post 90 indicate the width between the cut proximal surface of the tibia and the cut distal surface of the femur so that an implant of the appropriate width can be inserted.

If it is desired to adjust the placement of the tibial cutting guide component 50, the drill bits which have been driven into the bone can be left in place and the tibial cutting guide component 50 can be moved forward, for example from a position in which the drill holes 54 marked 0 (seen in FIG. 4) are placed over the drill bits, such that drill holes 54 marked +2 or +4, indicating forward movement of the cutting guide component 50 a distance of 2 or 4 millimeters, are placed over the drill bits, or moved backward such that drill holes 54 marked −2 or −4, indicating backward movement of the cutting guide component 50 a distance of 2 or 4 millimeters, are placed over the drill bits. It is thus not necessary to drill new drill bits or screws into the bone to move the cutting guide a predetermined distance.

After the appropriate cut is made on the tibia, cutting the anterior cruciate ligament, the femoral component 10 is removed from the patient's knee by releasing securing knob 52 and lifting out femoral component 10. A template for making anchoring holes for the prosthesis as known to the art in the cut tibial surface is then placed over the cut surface with its handle lined up with template alignment mark 51 on tibial cutting guide component 50. After the anchoring holes are made, the tibial cutting guide 50 and its drill bits or screws are removed from the bone and an appropriate prosthesis is fitted into the space between the cut surfaces of the distal femur and proximal tibia according to standard arthroplasty procedures.

In one embodiment of the invention using the alignment attachment 30 of the rotation alignment instrument of this invention, the insertion pins 38 on the alignment rod base 36 are inserted into pin receiving holes 39 of bracket 47. The device is then aligned with alignment rod 32 parallel with the long axis of the femur. The femoral component 10 is placed with femoral ledge 70 abutting the prepared flat anterior surface of the patient's femur which has previously been prepared by cutting at right angles to the long axis of the femur, as is known to the art. The alignment rod 32 is pulled down so that the tibia can be lined up with the long axis thereof parallel to the alignment rod 32. Rather than equalizing the tension on both sides of the knee by turning adjustment knobs 80, these knobs are turned until the tibial long axis lines up with the alignment rod. Alternatively, the adjustment knobs may be turned so that tibial leaves 60 remain parallel with femoral leaves 40, and the space between them remains rectangular in shape.

While this invention has been illustrated and described by means of specific embodiments, it is to be understood that numerous changes and modifications may be made therein without departing from the spirit and scope of the invention as defined in the appended claims.

I claim:

1. A rotation alignment device for positioning the tibia relative to the femur of a patient prior to placement of prosthetic knee components, comprising:

a femoral component having femoral leaves separated by a space large enough to accommodate the patient's anterior cruciate ligament, the femoral leaves being in the form of plates having proximal and distal surfaces, the proximal surfaces adapted to abut a patient's distal femur in use;

tibial leaves corresponding to the femoral leaves also being in the form of plates cooperatively engaged with the femoral component and having flat proximal surfaces parallel to the distal surfaces of the femoral leaves;

means for adjusting and maintaining a desired distance between the distal surface of each femoral leaf and the proximal surface of the corresponding tibial leaf;

means for preventing disengagement of the tibial leaves from the femoral leaves in use;

sheath means attached to the femoral leaves and leg barrel means attached to the tibial leaves, wherein the leg barrel means are slidably engaged with the sheath means and wherein the means for preventing disengagement of the tibial and femoral leaves comprises a keyway on the outer surface of the leg barrel means and a key on the inner surface of the sheath means.

2. A rotation alignment device for positioning the tibia relative to the femur of a patient prior to placement of prosthetic knee components, comprising:
- a femoral component having femoral leaves separated by a space large enough to accommodate the patient's anterior cruciate ligament, the femoral leaves being in the form of plates having proximal and distal surfaces, the proximal surfaces adapted to abut a patient's distal femur in use;
- tibial leaves corresponding to the femoral leaves also being in the form of plates cooperatively engaged with the femoral component and having flat proximal surfaces parallel to the distal surfaces of the femoral leaves;
- means for adjusting and maintaining a desired distance between the distal surface of each femoral leaf and the proximal surface of the corresponding tibial leaf;
- a femoral ledge at approximately right angles to the femoral leaves adapted to be placed against the flattened anterior surface of the distal femur in use.

3. The device of claim 2 comprising separate means for adjusting and maintaining a desired distance between each femoral leaf and the corresponding tibial leaf.

4. The device of claim 3 comprising means for equalizing the tension exerted against the tibia by each tibial leaf.

5. The device of claim 4 comprising spring means compressible by the threaded shaft means.

6. The device of claim 2 wherein the adjustment means comprise shaft means threadably attached to the femoral component for controllably pushing the tibial leaves apart from the femoral leaves.

7. The device of claim 6 comprising calibrated shafts attached to the tibial leaves disposed within the threaded shaft means.

8. The device of claim 2 comprising means for preventing disengagement of the tibial leaves from the femoral leaves in use.

9. The device of claim 2 also comprising a tibial cutting guide component removably attachable to the femoral component.

10. The device of claim 9 wherein the tibial cutting guide component comprises a saw guide groove.

11. The device of claim 9 wherein the tibial cutting guide component comprises attachment means for attaching the guide to the patient's tibia.

12. The device of claim 2 also comprising an alignment attachment comprising an alignment rod removably attachable to the femoral component.

13. The device of claim 2 comprising a separation post comprising separation marks adapted for measuring the distance between the femoral leaves and the tibial leaves in use.

14. A method for preparing a patient's femur and tibia for placement of prosthetic knee components using a rotation alignment device of claim 9 comprising femoral and tibial components, comprising:
- placing femoral leaves of the femoral component of the alignment device having parallel femoral and tibial leaves and a femoral ledge at approximately right angles to the femoral leaves adjacent the patient's distal femur, with the femoral ledge adjacent the flattened anterior surface of the distal femur, and placing the tibial leaves adjacent the patient's proximal tibia without cutting the patient's anterior cruciate ligament;
- separating each femoral leaf from its corresponding tibial leaf a desired distance;
- placing a tibial cutting guide component comprising a saw groove adjacent to both tibial leaves and to the patient's anterior tibial cortex; and
- cutting the patient's tibia with a saw placed in the saw groove.

15. The method of claim 14 wherein each femoral leaf is separated from its corresponding tibial leaf a different desired distance.

16. The method of claim 14 wherein the tension on each tibial leaf to keep it separate from its corresponding femoral leaf is the same.

17. The method of claim 14 wherein the desired distance of each tibial leaf from its corresponding femoral leaf is adjusted so that the long axes of the patient's femur and tibia are aligned with each other.

18. The method of claim 14 comprising using a calibrated separation post to attach the tibial cutting guide component to the femoral component and determining the width of the prosthetic knee component to be placed in the patient from the reading on the separation post.

19. A method of making a rotation alignment device of claim 9 for aligning a patient's tibia and femur prior to insertion of prosthetic knee components comprising:
- providing a femoral component comprising two femoral leaves separated from each other by an inlet large enough to accommodate a patient's anterior cruciate ligament, a femoral ledge at approximately right angles to the femoral leaves, and two sheaths, each sheath disposed at an approximate right angle to one of the femoral leaves;
- providing two tibial components each comprising a tibial leaf and a shaft at approximately right angles to the tibial leaf;
- slidably engaging the shafts of the tibial components with the sheaths of the femoral component, whereby each tibial leaf is adjacent and parallel to a corresponding femoral leaf; and
- providing each sheath with means for separately moving each tibial leaf a desired distance from its corresponding femoral leaf, means for equalizing the tension on each tibial leaf, and maintaining the position of the separated leaves.

* * * * *

UNITED STATES PATENT AND TRADEMARK OFFICE
CERTIFICATE OF CORRECTION

PATENT NO. : 5,669,914

DATED : September 23, 1997

INVENTOR(S) : Donald G. Eckhoff

It is certified that error appears in the above-identified patent and that said Letters Patent is hereby corrected as shown below:

In column 11, line 56 of claim 14, delete "claim 9" and replace with --claim 2--.

In column 12, line 34 of claim 19, delete "claim 9" and replace with --claim 2--.

Signed and Sealed this

Thirtieth Day of December, 1997

Attest:

BRUCE LEHMAN

Attesting Officer

Commissioner of Patents and Trademarks